(12) United States Patent
Bernhardt et al.

(10) Patent No.: US 9,272,963 B2
(45) Date of Patent: Mar. 1, 2016

(54) FINAL BIOGAS PURIFICATION PROCESS

(75) Inventors: Jean-Marc Bernhardt, La Buisse (FR); Pierre Briend, Seyssinet (FR); David Grillot, Rives (FR); Elise Renou, Paris (FR); Simon Saulquin, Grenoble (FR); Olivier Weitten, Grenoble (FR)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 32 days.

(21) Appl. No.: 13/996,773

(22) PCT Filed: Dec. 21, 2011

(86) PCT No.: PCT/EP2011/073655
§ 371 (c)(1),
(2), (4) Date: Jun. 21, 2013

(87) PCT Pub. No.: WO2012/085128
PCT Pub. Date: Jun. 28, 2012

(65) Prior Publication Data
US 2013/0269523 A1    Oct. 17, 2013

(30) Foreign Application Priority Data
Dec. 21, 2010   (FR) ................................ 10 60988

(51) Int. Cl.
*B01D 53/04* (2006.01)
*C07C 7/12* (2006.01)
*B01D 53/047* (2006.01)

(52) U.S. Cl.
CPC ............. *C07C 7/12* (2013.01); *B01D 53/0438* (2013.01); *B01D 53/0462* (2013.01); *B01D 53/0476* (2013.01); *B01D 2256/24* (2013.01); *B01D 2257/504* (2013.01); *B01D 2257/80* (2013.01); *Y02C 10/08* (2013.01)

(58) Field of Classification Search
CPC ............... B01D 53/04; B01D 53/0438; B01D 53/0462; B01D 53/0476; B01D 2256/24; B01D 2257/504; B01D 2257/80; C07C 7/12; Y02C 10/08
USPC ...................... 95/96, 106, 114, 115, 139, 148
See application file for complete search history.

(56) References Cited

U.S. PATENT DOCUMENTS 3,594,983 A * 7/1971 Yearout ............................. 95/97
6,103,143 A * 8/2000 Sircar et al. ................... 252/373

(Continued)

FOREIGN PATENT DOCUMENTS

| CN | 101352638 | 1/2009 |
|---|---|---|
| EP | 1291067 A2 | 3/2003 |
| FR | 818151 A | 9/1937 |
| WO | WO 2009 061836 | 5/2009 |

OTHER PUBLICATIONS

PCT/EP2011/073655, International Search Report, Mar. 23, 2012.

(Continued)

*Primary Examiner* — Frank Lawrence
(74) *Attorney, Agent, or Firm* — Elwood L. Haynes

(57) ABSTRACT

The present invention relates to a process for the purification by adsorption of a feed flow rich in methane and comprising at least carbon dioxide.

9 Claims, 5 Drawing Sheets

(56) References Cited

U.S. PATENT DOCUMENTS

| | | |
|---|---|---|
| 6,508,862 B1 | 1/2003 | Tonkovich et al. |
| 2008/0289497 A1 | 11/2008 | Barclay et al. |
| 2008/0314245 A1 | 12/2008 | Hershkowitz et al. |
| 2011/0041689 A1 | 2/2011 | Hansen et al. |
| 2015/0005563 A1* | 1/2015 | Barclay et al. ............... 585/822 |

OTHER PUBLICATIONS

FR 1060988, Search Report and Written Opinion, Jul. 26, 2011.

Written Opinion for corresponding PCT/EP2011/073655, Apr. 4, 2012.

* cited by examiner

FINAL BIOGAS PURIFICATION PROCESS

CROSS-REFERENCE TO RELATED APPLICATIONS

This application is a §371 of International PCT Application PCT/EP2011/073655, filed Dec. 21, 2011, which claims §119(a) foreign priority to French patent application 1060988, filed Dec. 21, 2010.

FIELD OF THE INVENTION

The present invention relates to a process for the purification by adsorption of a feed flow rich in methane and comprising at least carbon dioxide.

BACKGROUND

It relates in particular to the final purification of biogas, with the aim of producing methane, preferably liquid methane; this is because liquefaction is a method of packaging methane which makes it possible to economically store it and transport it.

Anaerobic (oxygen-free) fermentation of organic waste gives off a gas essentially consisting of methane and carbon dioxide, known as biogas. This process is developing fast, both in order to limit the emissions of greenhouse gases into the atmosphere but also to make use of the biogas thus produced, which is an appreciable energy source.

Biogas is intended in particular to feed electrical turbines or to act as fuel for vehicles.

Resulting from anaerobic fermentation, biogas comprises $CO_2$ and $CH_4$ in respective proportions depending on the nature of the materials fermented; in general, the biogas produced comprises between 55% and 65% of methane.

Biogas, once purified from its carbon dioxide, from its water and from its hydrogen sulphide $H_2S$, can be made use of economically as methane, in particular as fuel.

As recalled above, liquefaction is a preferred method of packaging methane, whether for storage purposes or transportation purposes. Any unit for the purification of $CO_2$-comprising biogas will thus require the inclusion, in its process, of a final purification of methane in order to remove, among other constituents, those which are incompatible with the liquefaction or another treatment requiring a change to cryogenic temperatures. It will be advisable in particular to limit the $CO_2$ concentration to a maximum content in fine of less than 100 ppm.

The final purification of methane resulting from biogas with the aim of producing liquid methane involves different processes known from the state of the art, which are pressure swing adsorption (PSA), temperature swing adsorption (TSA) or washing with amines.

These normal adsorption techniques involve, for the regeneration of adsorbents, large amounts of gas. However, the production sites for biogas (digester, landfill sites, and the like) generally do not have available large amounts of clean gases (pure $CH_4$, $N_2$) for the regeneration of the adsorbers.

Furthermore, when the amount of $CO_2$ in the biogas is significant (>1%), the exothermicity of the adsorption heats up the adsorbent, thus damaging its adsorption capacity, and it is thus essential to have available efficient cooling; during the regeneration of the adsorbent, it is necessary, on the contrary, to contribute a large amount of heat for the desorption of the impurities.

The circulation in a closed loop with reheating during the regeneration phase is not effective as the circulating gas very rapidly becomes loaded with impurities ($CO_2$) and distributes the impurities over the whole of the adsorbent bed. The residual content of impurities is then too high to achieve a gas quality compatible with liquefaction (<100 ppm). A flushing gas is necessary.

In order to be able to produce purified methane while operating the plant continuously, use is made, in a known way, of two adsorbers in parallel, one being in the adsorption phase while the other is in the desorption phase.

There is known, from US 2008/0289497, a system for purifying methane for the purpose of liquefying it, and in particular for removing $CO_2$, using three adsorbents. While one is in the adsorption phase, the second is in the desorption phase and the third is cooled, the presence of three adsorbers making possible heat transfers.

While the above system makes it possible to limit the external energy contribution, it requires, however, the use of three adsorbers in parallel, which generates additional costs in comparison with a conventional plant using two adsorbers. The problem which is posed is thus that of providing a solution for purifying impure methane, in particular resulting from biogas, so as to produce methane having a purity compatible with liquefaction, while limiting the costs, both in terms of capital costs and in terms of operating costs—no third adsorber, reduced consumption of utilities, in particular of energy.

The term "impure methane" (or "flow rich in methane") is understood to mean methane having a $CO_2$ content of less than 5%, preferably of less than 2%.

The term "purified methane" (or "methane having a purity compatible with liquefaction") is understood to mean, according to the invention, methane exhibiting a carbon dioxide content of less than 100 ppm, preferably less than 50 ppm.

SUMMARY OF THE INVENTION

According to a subject-matter of the invention, a process for the purification by adsorption of a feed flow rich in methane and comprising at least carbon dioxide, employing two exchangers-adsorbers (Ads1, Ads2) of shell-and-tube type, is provided, which process comprises at least the following stages:

1) sending the said feed flow to an exchanger-adsorber of the shell-and-tube type provided with an adsorbent in the tubes and with a cooling thermal fluid circulating in the shell of the said exchanger-adsorber in order to produce a purified flow depleted (at least) in carbon dioxide, with respect to the feed flow, then 2) circulating a hot thermal fluid in the shell, so as to desorb the impurities retained by the adsorbent and to regenerate the latter, in which stages 1) and 2) are carried out alternately on the two exchangers-adsorbers installed in parallel, the feed flow being sent to one of the exchangers-adsorbers while the second is in the regeneration phase and then to the second when the first is in the regeneration phase, and additionally comprising, at the start of stage 2), a stage of gradual reheating of the exchanger-adsorber to be regenerated and, at the end of stage 2), a stage of gradual cooling of the regenerated exchanger-adsorber, these stages of gradual bringing to temperature of the exchangers-adsorbers comprising at least exchanges of thermal fluid between the shell of the exchanger-adsorber, at least two storage means (S1, S2)—with a storage capacity comparable to the capacity of the shell—, intermediately storing the thermal fluid at variable temperatures, and a storage/heating means (C) with a capacity greater than the capacity of the shell, capable of providing additional heating of the thermal fluid for the implementation of stage 2).

The technology provided for the two exchangers-adsorbers is of the shell-and-tube exchanger type comprising the adsorbent in the tubes and a thermal fluid circulating in the shell. The advantage is to benefit, via the surface area of the tubes, from a high heat-exchange capacity essential to the alternation of the operating thermal systems of the process.

The combination of the two exchangers-adsorbers, installed in parallel, one operating in the adsorption phase while the other is in the regeneration phase, ensures the continuous production of purified gas. Throughout the adsorption phase according to stage 1, a cold thermal fluid circulates in the shell, in order to retain a low temperature in the adsorbent and thus to retain its adsorbent properties. When the adsorbent is saturated in impurities, it is necessary to proceed to the regeneration of the adsorbent. As the regeneration is carried out under hot conditions, the solution of the invention makes it possible to limit the cost of this regeneration. This is because the solution provided makes it possible to carry out the adsorption of the impurities while continuously cooling the adsorbent of the exchanger-adsorber in the adsorption phase and to carry out, over the same time, the regeneration of the adsorbent of a second exchanger-adsorber, comprising the heating in successive stages of the adsorbent—using for this heat sources carefully arranged so as to minimize the consumption of energy of the regeneration—until the adsorbent is regenerated, followed by the cooling, itself also in successive stages, of the adsorber. This cooling according to the invention prepares the exchanger-adsorber Ads2 for the following adsorption stage and prepares the various heating and storage means for the regeneration stage, this time applied to Ads1.

A preferred thermal fluid is water.

Preferably, the gradual reheating of the exchanger-adsorber Ads2 at the beginning of the regeneration stage comprises at least the stages of:
  prior to the reheating:
  (i) arranging:
    cold thermal fluid in the shell of the exchanger-adsorber at a temperature lower than or of the order of ambient temperature,
    hot thermal fluid in the storage means S1 at a temperature greater than 110° C.,
    tepid thermal fluid in the storage means S2 at a temperature of between 70° C. and 110° C., preferably between 80° C. and 100° C.,
    hot thermal fluid in the storage/heating means C at a temperature greater than 115° C., preferably of the order of 130° C.,
  (ii) circulation of cold thermal fluid in the shell of the exchanger-adsorber Ads2 in the adsorption phase according to stage 1), in order to ensure the maintenance of the cold during the said stage 1), then gradual reheating by:
  (iii) exchange, at the end of stage 1), of the cold thermal fluid present in the shell of Ads2 with the tepid fluid present in the storage means S2; S2 then comprises cold fluid,
  (iv) reheating the fluid present in the shell of Ads2 by exchange of heat via an exchanger 12 up to a tepid fluid temperature of between 80° C. and 105° C., preferably of the order of 100° C.,
  (v) exchange of tepid thermal fluid present in the shell of Ads2 on conclusion of stage (iv) with the hot fluid present in the storage means S1,
  (vi) reheating the hot thermal fluid present in the shell of Ads2 by circulation of fluid between the shell and the storage/heating means (C) up to the end of the regeneration according to stage 2).

During the regeneration phase, a hot thermal fluid—preferably water superheated to a temperature of greater than 110° C., more preferably of the order of 130° C.—thus circulates in the shell of the adsorber in the regeneration phase in order to contribute the heat necessary for the desorption of the impurities.

The end of the phase of regeneration of the adsorbent of Ads2 marks the end of the circulation of hot fluid between Ads2 and the vessel C.

The use of an additional heating means HX, in order to moderately reheat the thermal fluid in the shell during stage (iv), is made necessary in order to compensate for the fall in temperature brought about by the reheating of the exchanger-adsorber.

Preferably, the gradual cooling of the regenerated exchanger-adsorber Ads2 on conclusion of stage 2) and prior to the adsorption according to stage 1) comprises at least the stages of:
  prior to the cooling:
  (vii) arranging:
    hot thermal fluid in the shell of the exchanger-adsorber Ads2, at a hot fluid temperature greater than 110° C., preferably between 115° C. and 130° C.,
    thermal fluid in the storage means S1 at a water temperature of the order of 100° C. to 110° C.,
    the cold thermal fluid in the storage means S2,
    the hot thermal fluid in the storage/heating means (C) at a temperature greater than 115° C., preferably of the order of 130° C.,
  and gradual cooling, including
  (viii) exchange of the thermal fluid present in the shell of Ads2 with the thermal fluid of the storage means S1; S1 then comprises hot thermal fluid,
  (ix) exchange of the tepid fluid present in Ads2 with the cold fluid present in the storage means S2,
  (x) reheating the fluid present in S2 by HX, so as to reconstitute the tepid storage according to stage (i),
  (xi) continuous cooling of Ads2 by cold thermal fluid.

According to the invention, bringing the exchangers-adsorbers to temperature between the adsorption and regeneration stages, that is to say the heating of the exchanger at the end of adsorption and the cooling of the exchanger at the end of regeneration, is carried out gradually, by successive stages of exchange of fluid between the shell and at least two storage means with a storage capacity comparable to the capacity of the shell, and a storage/heating means (C) with a much greater capacity, preferably at least double the capacity of the shell, capable of providing additional heating of the thermal fluid for the implementation of stage 2). The storage means intermediately store the thermal fluid (preferably water) at variable temperatures—one of the storage means alternately storing cold water and tepid water (i.e., at a temperature of between 80° C. and 100° C.) and the second storage means alternately storing tepid water (i.e., at a temperature of between 80° C. and 100° C.) and hot water (i.e., at a temperature between 100° C. and 130° C.)—. The storage/heating means is preferably an additional water heater, connected to the exchanger-adsorber in the regeneration phase; it ensures the maintenance of the hot water temperature in the shell during the regeneration stage 2).

According to preferred alternative forms of the invention, the latter can relate to a process in which:

During the regeneration stage, the impurities are advantageously withdrawn from the adsorbent by vacuum pumping at a pressure preferably of between 100 and 200 mbara, so as to combine a pressure swing with the temperature swing.

As the adsorption is preferably carried out at a pressure of between 7 and 15 bar, it is necessary, in order to change from the adsorption mode to the regeneration mode, to depressurize the exchanger-adsorber; in order to increase the impact of the reduction in pressure on the regeneration, an inert gas, generally nitrogen, can be injected on the opposite side from the vacuum pump, so as to dilute the fraction of impurity in the desorbed gas and to thus reduce its partial pressure.

Advantageously, the repressurization of the exchanger-adsorber is carried out at the same time as the cooling, thus facilitating the cooling.

The cold fluid is preferably withdrawn from the general cooling system of the site.

The storage/heating means C is advantageously heated by an electrical heating resistor.

The thermal fluid exiting from the various storage means is circulated via circulation pumps and/or is forced with the incoming thermal fluid into the said storage means.

The external source heating the storage/heating vessel C can be an electrical resistor incorporated in the circuit in order to contribute the remaining heat necessary for the regeneration for a time sufficient to ensure the complete reheating of the adsorbent by conduction, to compensate for the heat losses in the desorbed gas and to contribute the heat necessary for the desorption (transfer of endothermic material).

Thus, advantageously, a portion of the heat necessary for the regeneration originates from a thermal fluid tank equipped with an electrical heating resistor.

In the case where the purified methane is liquefied, an additional energy contribution is obtained by exchange of heat with the cycle gas of the liquefier in a step of the final exchanger of the compressor which will make possible a consequent increase in the temperature. This heat contribution is used, inter alia, in stage (iv); the exchanger is identified therein as component 12.

BRIEF DESCRIPTION OF THE FIGURES

The invention will now be described with reference to an implementational example of the invention and to the appended figures, of which.

The numbers in bold in the text hereinafter repeat the reference numbers of the components in the figures; for a better understanding of the progression of the process, the components can also be identified by which can combine letters and numbers. The correspondence between the two methods of identification is specified in the text below.

DETAILED DESCRIPTION OF THE INVENTION

Figure 1:
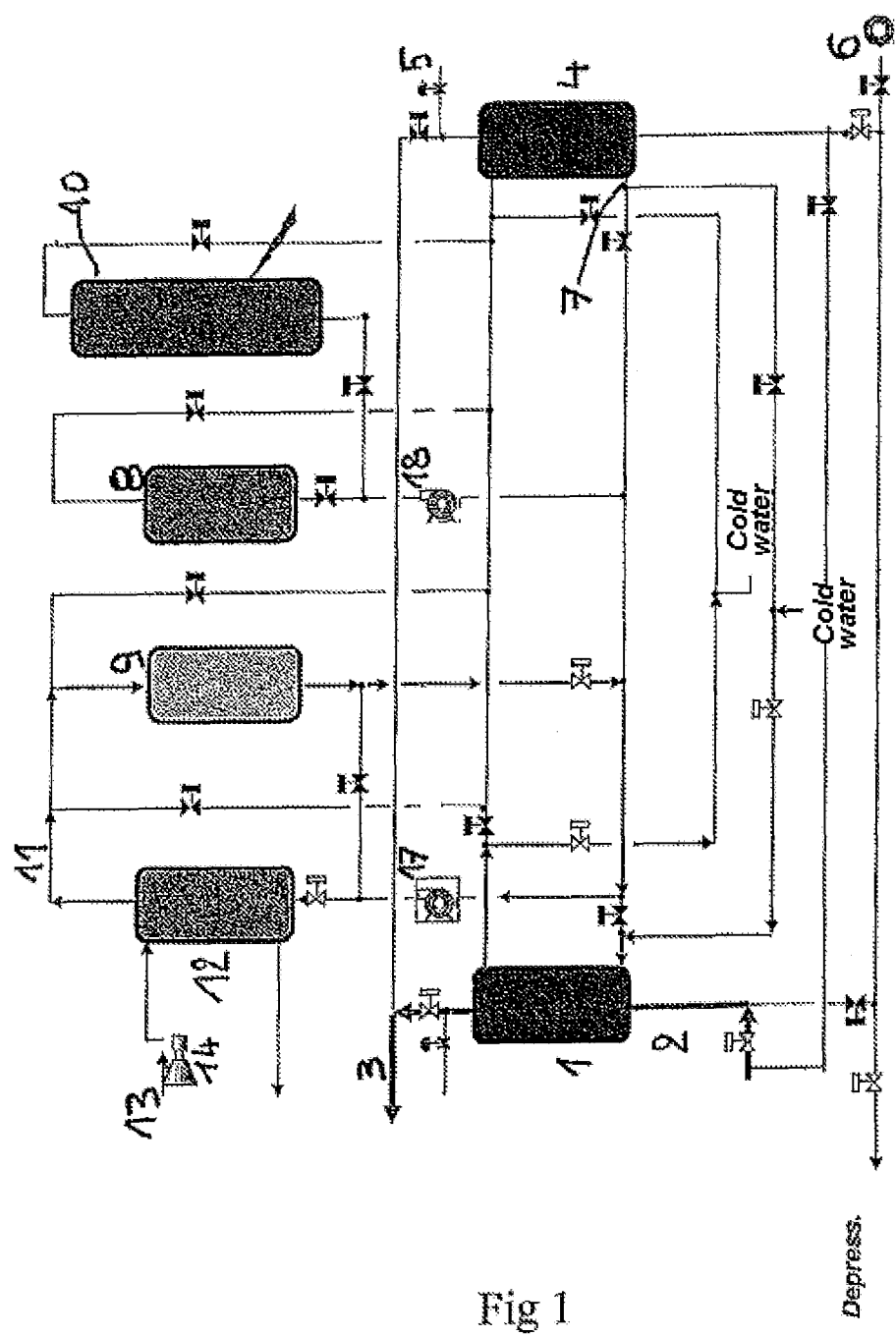
FIG. 1 diagrammatically represents a plant for the purification of biogas according to the invention, FIGS. 2a to 2g schematize stages of heating and cooling the exchanger-adsorber Ads2 of the plant of FIG. 1.

The plant of FIG. 1 operates in the following way:
the exchanger-adsorber Ads2 or Ads1 (respectively 1 or 4) is, when it is in adsorption mode, fed with impure gas 2 and produces pure gas 3; the regeneration of the other exchanger-adsorber is carried out during the adsorption phase of the first, Ads1 and Ads2 can be fed:
with elution nitrogen gas GN2 5; the desorbed flow is pumped via the vacuum pump 6,
with water at variable temperature originating from the receiver S1 8, from the receiver S2 9 and from the storage/heating means 10,
with hot water 11 originating from the exchanger HX 12, which exchanges with the hot gas GN2 13 compressed in the compressor of the liquefaction cycle 14 (methane liquefaction cycle, not represented),
with cold water 15 originating from the cooling circuit of the plant,
circulation water pumps 17 and 18 which make possible transfers of water,
in addition (not represented), a circuit makes possible the depressurization of the exchanger-adsorber at the beginning of regeneration and a separate circuit makes possible the repressurization with process gas of the regenerated adsorber.

An example of the application of the invention is described below in connection with FIG. 1 and FIGS. 2a to 2g.

The adsorption takes place alternately in the two exchangers-adsorbers 1 and 4 (of shell-and-tube type, it is essential to operate them by circulation of water at controlled temperatures in the shell).

The regeneration process according to the invention is designed to limit the consumption of electrical energy of 10 (vessel C).

The principle provided consists in employing:
the vessel C, which stores 2 m$^3$ of water and electrically reheats the water from 110° C. to 130° C., approximately;
another heat source which is the gas 13 at the outlet of a compressor 14. The gas 13 is used in the precooler exchanger 12 (HX) to reheat the water and to obtain tepid water up to 100° C.;
the hot water receiver 8 (S1); it alternately stores 1 m$^3$ of hot water (110° C. to 120° C.) or of tepid water 100° C.);
the tepid water receiver 9 (S2); it alternately stores tepid water, which has been reheated by HX to 100° C., or cold water at approximately 30° C. originating from Ads1 or Ads2 after adsorption.

The stages of gradually bringing to temperature are described below for Ads2; they are similar for Ads1.

Figure 2A:
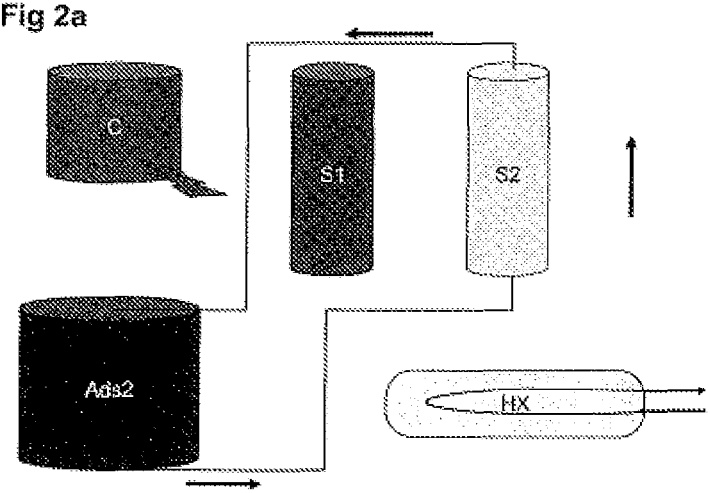

FIG. 2a schematizes stage iii of the process, during which Ads2 exchanges 0.9 m$^3$ of water at 20° C. present in the shell with 0.9 m$^3$ of water at 100° C. present in S2. This is the first stage of preheating the adsorber with the tepid water of S2 (the water initially present in S2 is the water resulting from the preceding regeneration cycle, that is to say from that of Ads1). The amount of heat transferred to Ads2 contributes essentially to the reheating of the construction materials of the exchanger-adsorber; the transfer of heat is very efficient as the thermal diffusivity of steel is very high; the water in Ads2 is then at 50° C. approximately.

Figure 2B:
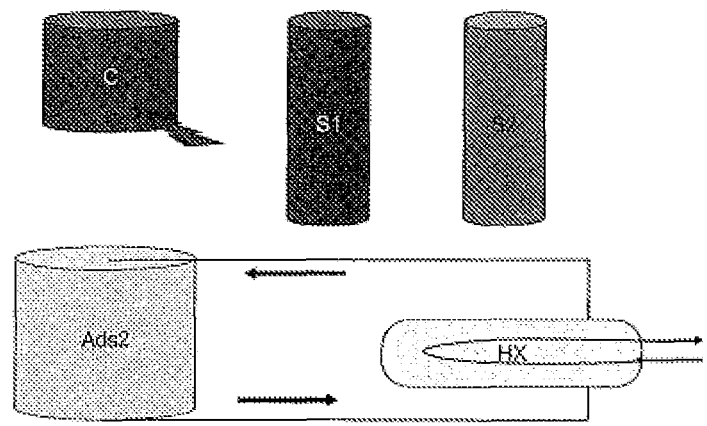

FIG. 2b schematizes stage iv of the process, during which water circulates in a loop between Ads2 and HX (the water initially present in HX is at a tepid water temperature of the order of 100° C. according to stage i). The water of Ads2 is thus brought to 90° C. approximately.

Figure 2C:
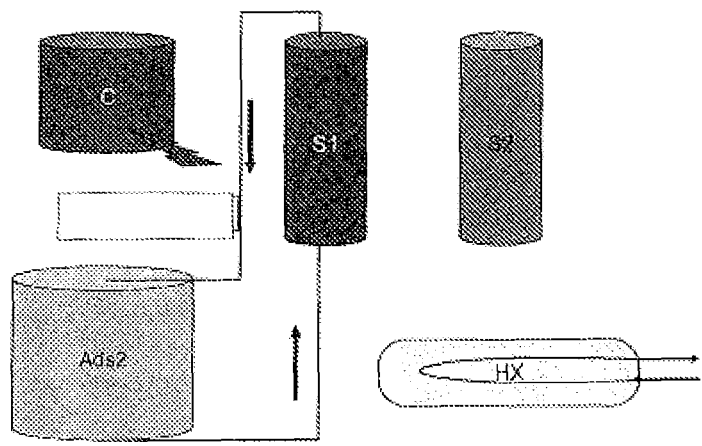

FIG. 2c schematizes stage v of the process, during which the tepid water present in the shell of Ads2 (90° C.) is exchanged with the hot water stored in S1 (the water initially present in 8 (S1) is at a hot water temperature of the order of 110° C. according to stage i).

Figure 2D:
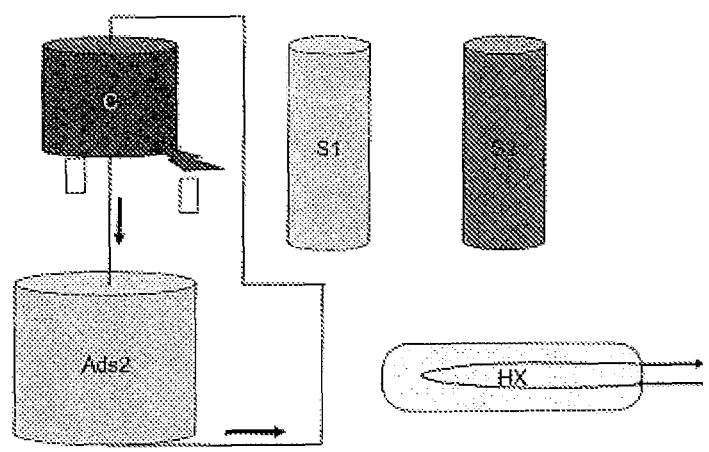

FIG. 2d schematizes stage vi of the process, during which hot water circulates from 10 (vessel C) to the shell of Ads2;

simultaneously, the water initially present in Ads2; simultaneously, the water driven from Ads2 circulates up to C. In order to ensure optimum reheating of the water in the shell, the volume circulated is greater than the volume of the shell (according to the example, 1.4 m³ of water at 130° C. circulates for a volume of the shell of the order of 0.9 m³).

The end of the phase of regeneration of the adsorbent of Ads2 is linked with the end of reheating of Ads2 by the vessel C.

The aim of the following stages is to cool the water present in the shell of Ads2 so that it is thermally operational for the adsorption stage of the following cycle.

Figure 2E:
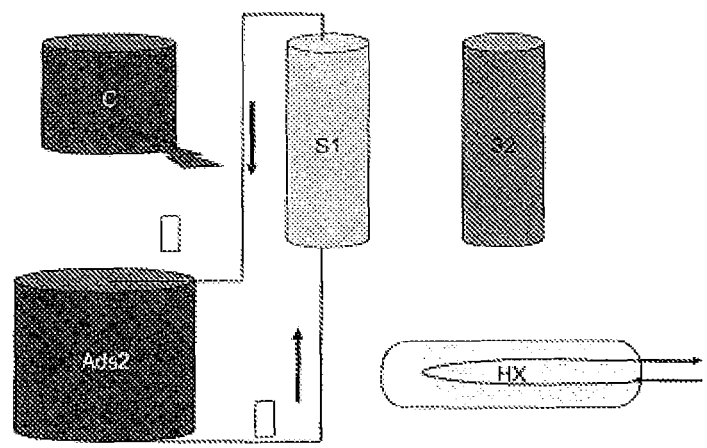

FIG. 2e thus schematizes stage vii of the process, during which the hot water of Ads2 (at approximately 120° C.) is exchanged with the tepid water of S1 (at approximately 100° C.). This stage thus makes it possible to cool the adsorber while retaining—in the storage means S1—the hot water which it contained for the needs internal to the process, and the like.

Figure 2F:
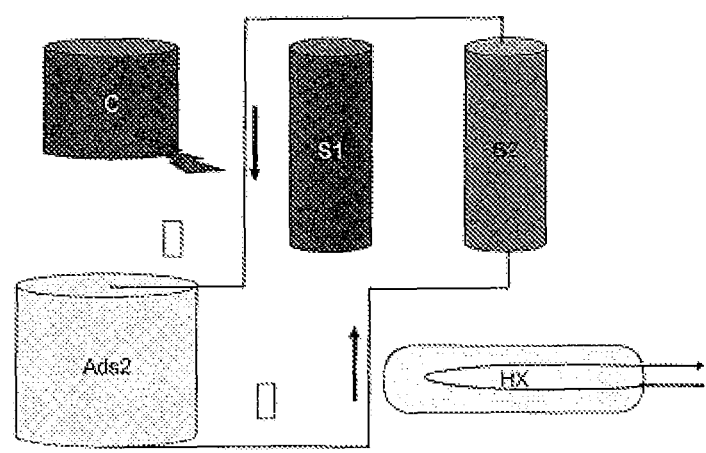

FIG. 2f schematizes stage viii of the process, during which the tepid water of Ads2 is exchanged with the cold water of S2, thus making it possible to continue the cooling of the exchanger-adsorber Ads2 while retaining—in the storage means S2—the tepid water which it contained for the needs internal to the process. In stage R6, in order to retain the energy present in the tepid water, it is exchanged with the water from Receiver-2 which contained cold water from the preceding transfer.

Figure 2G:
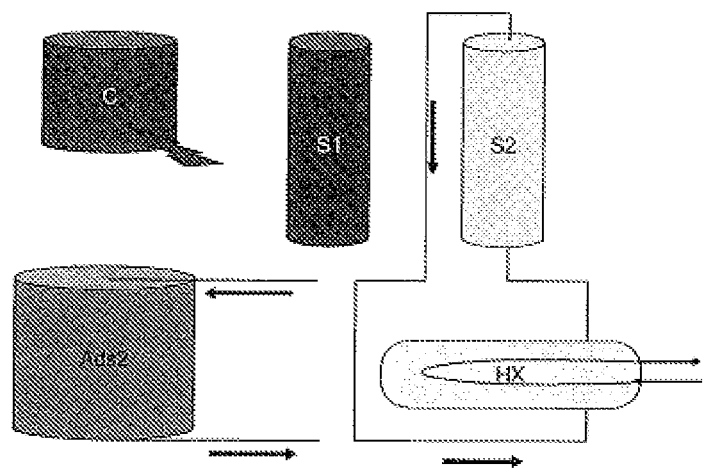

Finally, FIG. 2g schematizes stage ix of final cooling of Ads2, which is obtained by circulation of cold water. During this stage, the water from the vessel S2 is reheated by circulation in a loop in HX.

At the same time as the phase of regeneration of 1 (Ads2) takes place, which involves the means 8, 9, 10, and 12—the regeneration phase comprising reheating, regeneration and cooling stages—, the adsorber 4 (Ads1) is in the adsorption phase. The end of the regeneration of Ads2 coincides with the end of the adsorption on Ads1; then, according to the process of the invention, Ads1 is regenerated while Ads2 is in the adsorption phase.

Two tests were carried out for the purposes of comparison, employing the following components:
common components:
  2 exchangers-adsorbers of shell-and-tube type, having one pass, exhibiting a shell volume of 0.88 m³, in which water circulates;
  1 pre-cooler exchanger HX of shell-and-tube type, having 2 passes, exhibiting a shell volume of 0.3 m³, in which water circulates;
  1 receiver S for storage of water with a volume of 1 m³;
  1 "water heater" C for the storage and heating of a volume of water of 2 m³;
for the test according to the invention, a second storage receiver of S type is added.

The tests carried out showed that the energy consumed to heat the water of the vessel C to 130° C. is 68 kW when just one receiver S is used, whereas the addition of an additional intermediate receiver of the same type S makes it possible to reduce the consumption to 23.3 kW (i.e., by a factor of approximately 3).

The invention has been described in the case where the thermal fluid is water; this has made it possible to specify certain data, in particular temperature ranges during the heating and cooling stages, but the use of other fluids can be envisaged, depending on the adsorption and regeneration techniques employed, it being understood that the principle of the invention lies in:

the use of two exchangers-adsorbers of shell-and-tube type alternately,
the use of a tepid/cold storage means and of a tepid/hot storage means, in addition to the storage/heating means C, in order to ensure the heating and the cooling of the adsorber in regeneration.

The invention cleverly uses the speed of the regeneration at high temperature in comparison with the adsorption, which gives the possibility of carrying out the circulations of thermal fluids at different temperatures and the successive heatings of the invention.

There are many advantages to the invention.

The use of two shell-and-tube exchangers with an adsorbent in the tubes and a thermal fluid outside, to which recourse is had during the adsorption and the regeneration, combined with the use of two intermediate storage means cleverly storing water at variable temperatures, thus exhibits numerous advantages, including:
  the possibility of using water as heat-exchange fluid, cooling water generally being widely available on site,
  the limitation on the consumption of electrical energy necessary for the regeneration via appropriate storages of thermal fluid (tepid water and hot water at two different temperatures), also via the use of a step of the final exchanger of compression of the cycle gas of the biogas liquefier.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A process for the purification by adsorption of a feed flow rich in methane and comprising at least carbon dioxide,
  employing a first exchanger-adsorber and a second exchanger-adsorber,
  first exchanger-adsorber and second exchanger adsorber being shell-and-tube type,
  first exchanger-adsorber and second exchanger adsorber comprising a shell side and a tube side,
  first exchanger-adsorber and second exchanger adsorber with an adsorbent in the tube side, and a cooling thermal fluid circulating in the shells side, the process comprising:
    1) during an adsorbing step, sending the feed flow to one of the exchanger-adsorbers thereby producing a purified flow depleted in carbon dioxide with respect to the feed flow,
    2) during a regeneration step, circulating a hot thermal fluid in the shell side of the exchanger-adsorber in step 1), so as to desorb the impurities retained by the adsorbent and thereby regenerate the adsorbent,
  wherein the first exchangers-adsorbers and second exchanger-adsorber are installed in parallel,
  alternately carrying out steps 1) and 2) on the at least two exchanger-adsorbers, further comprising,
  gradually reheating the exchanger-adsorber to be regenerated at the start of step 2), and,
  gradually cooling the exchanger-adsorber at the end of stage 2),
  wherein the gradual heating and cooling comprises exchanging thermal fluid between the shell of the exchanger-adsorber, at least two storage means, each with a storage capacity comparable to the capacity of the shell side, intermediately storing the thermal fluid at variable temperatures, and a storage/heating means with a capacity greater than the capacity of the shell side, with the storage/heating means being capable of providing additional heating of the thermal fluid for the implementation of stage 2).

2. The process of claim 1, wherein the thermal fluid is water.

3. The process of claim 1, wherein the gradual reheating of the exchanger-adsorber at the beginning of the regeneration stage comprises the steps of:

prior to the reheating:

(i) arranging:
cold thermal fluid in the shell of the exchanger-adsorber at a temperature lower than or of the order of ambient temperature,
hot thermal fluid in a first storage means at a temperature greater than 110° C.,
tepid thermal fluid in a second storage means at a temperature of between 70° C. and 110° C.,
hot thermal fluid in the storage/heating means C at a temperature greater than 115° C., (ii) circulation of cold thermal fluid in the shell of the exchanger-adsorber in the adsorption phase according to stage 1), in order to ensure the maintenance of the cold during the said stage 1), gradual reheating by:

(iii) exchange, at the end of stage 1), of cold thermal fluid present in the shell of exchanger-adsorber with tepid thermal fluid present in the second storage means, the second storage means then comprises cold thermal fluid, (iv) reheating the thermal fluid present in the shell of exchanger-adsorber by exchange of heat via an exchanger up to a tepid thermal fluid temperature of between 80° C. and 105° C., (v) exchange of tepid thermal fluid present in the shell of exchanger-adsorber on conclusion of stage (iv) with the hot thermal fluid present in the first storage means, (vi) reheating the hot thermal fluid present in the shell of the second exchanger-adsorber by circulation of thermal fluid between the shell and the storage/heating means up to the end of the regeneration according to stage 2).

4. The process of claim 3, wherein the gradual cooling of the regenerated exchanger-adsorber on conclusion of stage 2) and prior to the adsorption according to stage 1) comprises at least the stages of:

prior to the cooling:

(vii) arranging:
hot thermal fluid in the shell of the exchanger-adsorber Ads2, at a hot fluid temperature greater than 110° C.,
thermal fluid in the storage means S1 at a water temperature of the order of 100° C. to 110° C.,
the cold thermal fluid in the storage means S2,
the hot thermal fluid in the storage/heating means is at a temperature greater than 115° C., and gradual cooling, including (viii) exchange of the thermal fluid present in the shell of Ads2 with the thermal fluid of the storage means S1; S1 then comprises hot thermal fluid, (ix) exchange of the tepid fluid present in Ads2 with the cold fluid present in the storage means S2, (x) reheating the fluid present in S2 by HX, so as to reconstitute the tepid storage according to stage (i), (xi) continuous cooling of Ads2 by cold thermal fluid.

5. The of claim 1, wherein the cold fluid is withdrawn from the general cooling system of the site.

6. The process of claim 1, wherein during stage 2), the impurities are withdrawn from the adsorbent by vacuum pumping, so as to combine a pressure swing with the temperature swing.

7. The process of claim 6, wherein an inert gas is injected on the opposite side from the vacuum pump, so as to dilute the impurity fraction in the desorbed gas and to thus reduce its partial pressure.

8. The process of claim 6, wherein the adsorption is carried out at a pressure of between 7 and 15 bar and the repressurization of the exchanger-adsorber is carried out at the same time as the cooling.

9. The process of claim 1, wherein the storage/heating means is heated by an electrical heating resistor.

* * * * *